(12) United States Patent
Hong et al.

(10) Patent No.: US 12,290,468 B2
(45) Date of Patent: May 6, 2025

(54) OSTOMY APPLIANCE

(71) Applicant: KOREA UNIVERSITY RESEARCH AND BUSINESS FOUNDATION, Seoul (KR)

(72) Inventors: Kwangdae Hong, Seoul (KR); Jaeyoung Kim, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 451 days.

(21) Appl. No.: 17/923,902

(22) PCT Filed: Mar. 3, 2021

(86) PCT No.: PCT/KR2021/002615
§ 371 (c)(1),
(2) Date: Nov. 7, 2022

(87) PCT Pub. No.: WO2021/230476
PCT Pub. Date: Nov. 18, 2021

(65) Prior Publication Data
US 2023/0210683 A1    Jul. 6, 2023

(30) Foreign Application Priority Data
May 15, 2020 (KR) .......................... 10-2020-0058238

(51) Int. Cl.
*A61F 5/44* (2006.01)
*A61F 5/445* (2006.01)

(52) U.S. Cl.
CPC ............ *A61F 5/4407* (2013.01); *A61F 5/445* (2013.01)

(58) Field of Classification Search
CPC ............ A61F 2005/4402; A61F 5/4407; A61F 5/445; A61F 5/448; B65F 2210/167;
(Continued)

(56) References Cited

U.S. PATENT DOCUMENTS 5,009,648 A * 4/1991 Aronoff .................. B32B 27/08
604/338
5,454,389 A * 10/1995 Hubbard ................. A61F 5/445
604/277
(Continued)

FOREIGN PATENT DOCUMENTS

CN          107284903 A  * 10/2017  ......... B65B 67/1244
GB          2516470 A    *  1/2015  ........... A61F 5/4404
(Continued)

OTHER PUBLICATIONS

Extended European Search Report in Application No. 21804255.4 dated May 24, 2024, 5 pages.
(Continued)

*Primary Examiner* — Adam Marcetich
*Assistant Examiner* — Ted Yang
(74) *Attorney, Agent, or Firm* — Park, Kim & Suh, LLC

(57) ABSTRACT

An ostomy appliance according to an embodiment of the present invention comprises: an attachment part attached to the skin of a user; a cover assembly part disposed on the top surface of the attachment part and continuously dispensing plastic film into which excrement flows; and a sealing part that is coupled to one side of the cover assembly part and thermally seals a portion of the dispensed plastic film.

11 Claims, 6 Drawing Sheets

(58) Field of Classification Search
CPC ........ B65F 2210/1675; B65F 2240/132; B65F 1/062; B65B 67/1277; B65B 9/15; B65B 9/18
See application file for complete search history.

(56) References Cited

U.S. PATENT DOCUMENTS

| | | | | |
|---|---|---|---|---|
| 6,065,272 | A * | 5/2000 | Lecomte | B65F 1/062 53/567 |
| 7,350,663 | B2 * | 4/2008 | Chomik | B65F 1/163 220/264 |
| 7,712,285 | B2 * | 5/2010 | Stravitz | B65F 1/062 53/77 |
| 7,958,704 | B2 * | 6/2011 | Stravitz | B65F 1/062 220/495.07 |
| 8,091,325 | B2 * | 1/2012 | Stravitz | B65B 9/15 53/567 |
| 8,635,838 | B2 * | 1/2014 | Dunn | B32B 27/28 53/284.7 |
| 9,883,964 | B2 | 2/2018 | Hanuka et al. | |
| 9,994,393 | B2 * | 6/2018 | Dunn | B65F 1/1615 |
| 2004/0030305 | A1 * | 2/2004 | Sakamoto | B29C 66/849 604/317 |
| 2005/0106706 | A1 * | 5/2005 | Chomik | A61N 1/325 220/252 |
| 2006/0074389 | A1 * | 4/2006 | Montgomery | A61F 5/445 604/339 |
| 2008/0004580 | A1 | 1/2008 | Mullejans et al. | |
| 2012/0136324 | A1 * | 5/2012 | Hanuka | A61F 5/441 604/318 |
| 2013/0079737 | A1 | 3/2013 | Hanuka et al. | |
| 2013/0116636 | A1 * | 5/2013 | Carrubba | A61F 5/448 604/318 |
| 2013/0253455 | A1 * | 9/2013 | Masters | A61F 5/445 604/332 |
| 2013/0298506 | A1 * | 11/2013 | Lucas | B65F 1/1426 53/574 |
| 2016/0031640 | A1 * | 2/2016 | Cudworth | B65F 1/062 53/545 |
| 2016/0113810 | A1 * | 4/2016 | Hanuka | A61F 5/445 604/335 |
| 2016/0151198 | A1 * | 6/2016 | Frampton | A61F 5/4404 604/340 |
| 2017/0291789 | A1 * | 10/2017 | Wong | B65F 1/068 |
| 2017/0360592 | A1 | 12/2017 | Carrubba | |
| 2021/0022909 | A1 * | 1/2021 | Torres Cardoso | A61F 5/441 |

FOREIGN PATENT DOCUMENTS

| | | | | |
|---|---|---|---|---|
| GB | 2518855 | A * | 4/2015 | ........... A61F 5/4404 |
| JP | H06-133894 | A | 5/1994 | |
| JP | H07-019208 | U | 4/1995 | |
| JP | H09-019451 | A | 1/1997 | |
| JP | H10-248867 | A | 9/1998 | |
| JP | 2002-011030 | A | 1/2002 | |
| JP | 2006-095321 | A | 4/2006 | |
| JP | 3826163 | B2 * | 9/2006 | |
| JP | 2007-505664 | A | 3/2007 | |
| JP | 2013-519408 | A | 5/2013 | |
| JP | 2015-091293 | A | 5/2015 | |
| JP | 2018011685 | A * | 1/2018 | |
| KR | 20-0431479 | Y1 | 11/2006 | |
| KR | 10-1079199 | B1 | 11/2011 | |
| KR | 10-2017-0011318 | A | 2/2017 | |
| KR | 10-1844957 | B1 | 4/2018 | |
| KR | 10-2033584 | B1 | 11/2019 | |

OTHER PUBLICATIONS

International Search Report in International Application No. PCT/KR2021/002615, dated Jun. 7, 2021, 2 pages.

* cited by examiner

OSTOMY APPLIANCE

CROSS-REFERENCE TO RELATED APPLICATIONS

This application is a National Phase Application of PCT International Application No. PCT/KR2021/002615, which was filed on Mar. 3, 2021, and which claims priority from Korean Patent Application No. 10-2020-0058238 filed on May 15, 2020. The disclosures of the above patent applications are incorporated herein by reference in their entirety.

TECHNICAL FIELD

The present invention relates to an ostomy appliance.

BACKGROUND ART

An ostomy procedure is a procedure that induces defecation by temporarily or permanently exposing a portion of an intestine to an abdominal wall due to a rectal cancer, a perineal disease, colovesical fistula, intestinal stenosis, peritonitis, and the like.

That is, when a function of a digestive system or a urination system is lost due to an accident or congenital and acquired diseases, and thus defecation and urine cannot be discharged smoothly, wastes in a human body may be discharged to the outside through an artificial ostomy procedure.

In this way, an artificial anus exposed to the outside is generally called an ostomy, and a patient who has undergone the ostomy procedure uses an ostomy appliance for convenience of excreting urine and defecation.

The ostomy appliance is roughly sold in the forms of a one-piece type and a two-piece type, the two-piece type ostomy appliance is configured with a skin barrier and a stoma bag attached to or detached from the skin barrier to contain the defecation and urine, the one-piece type ostomy appliance includes the skin barrier and the stoma bag which are integrally configured, and thus it is easy to attach the ostomy appliance.

However, the ostomy appliance has the following problems.

Both types of the ostomy appliances according to the related art have the stoma bags that contain urine and defecation. In this case, a distal end of the stoma bag is opened to discharge the urine and defecation contained therein. In this process, an unsanitary problem may occur in which the urine and defecation come into contact with hands and clothes of the patient or guardian.

In addition, in the ostomy appliance according to the related art, since the urine and defecation should be repeatedly discharged, there is a limitation in that the above problem occurs continuously.

DETAILED DESCRIPTION OF THE INVENTION

Technical Problem

Embodiments of the present invention are proposed to solve the above problems, and provide an ostomy appliance capable of overcoming unsanitary limitations of the ostomy appliance by continuously supplying a disposable vinyl bag, and at the same time, shielding a lower end of the vinyl bag.

Technical Solution

An ostomy appliance according to an embodiment of the present invention includes an attachment part attached to a skin of a user, a cover assembly part which is disposed on an upper surface of the attachment part and through which a vinyl sheet into which excretion is introduced is continuously discharged, and a sealing part coupled to one side of the cover assembly part and configured to heat-seal a portion of the discharged vinyl sheet.

Further, the cover assembly part may be formed in a ring shape having a hollow in a center thereof and may be disposed to be attached to or detached from the upper surface of the attachment part.

Further, the cover assembly part may include a body portion having an inner space so that the vinyl sheet is accommodated, a ring-shaped tube portion which is disposed in the inner space of the body portion and around which the vinyl sheet is wound, and a cover portion configured to shield an inner edge portion of the body portion.

Further, a discharge groove may be formed between the body portion and the cover portion in a circumferential direction, and the vinyl sheet may be discharged through pulling of a user.

Further, the vinyl sheet may be formed in a cylindrical shape in which an upper end and a lower end are open, may be folded flat, and may be wound around the ring-shaped tube portion, the vinyl sheet may be provided with perforated lines at preset intervals and divided into a plurality of unit vinyl sheets, and the unit vinyl sheets may be continuously connected in the same standard.

Further, the sealing part may include a sealing support portion hinge-coupled to one side of an outer edge portion of the body portion and rotated in a direction perpendicular to the body portion, and a sealing insulation portion disposed at an upper end of the sealing support portion.

Further, the sealing insulation portion may include a first sealing insulation portion formed such that a heating portion configured to heat-seal a portion of the unit vinyl sheet is mounted on one side surface thereof, and a pressing portion positioned to be engaged with the heating portion is mounted on a surface facing the one side surface of the first sealing insulation portion.

Further, the heating portion may be mounted to protrude more than the one side surface of the first sealing insulation portion.

Further, the heating portion may be divided into a first heater and a second heater which are dividedly mounted in a central portion of the one side surface of the first sealing insulation portion at a predetermined separation region.

Further, the vinyl sheet may be fitted in a gap between the first sealing insulation portion and the second sealing insulation portion, the perforated line of the fitted vinyl may be positioned between the first heater and the second heater, and portions of the unit vinyl sheets adjacent to each other with respect to the perforated line may be simultaneously heat-sealed.

Advantageous Effects of the Invention

An ostomy appliance according to embodiments of the present invention may overcome unsanitary limitations of the ostomy appliance by continuously supplying a disposable vinyl bag, and at the same time, shielding a lower end of the vinyl bag.

BEST MODE

Figure 1:
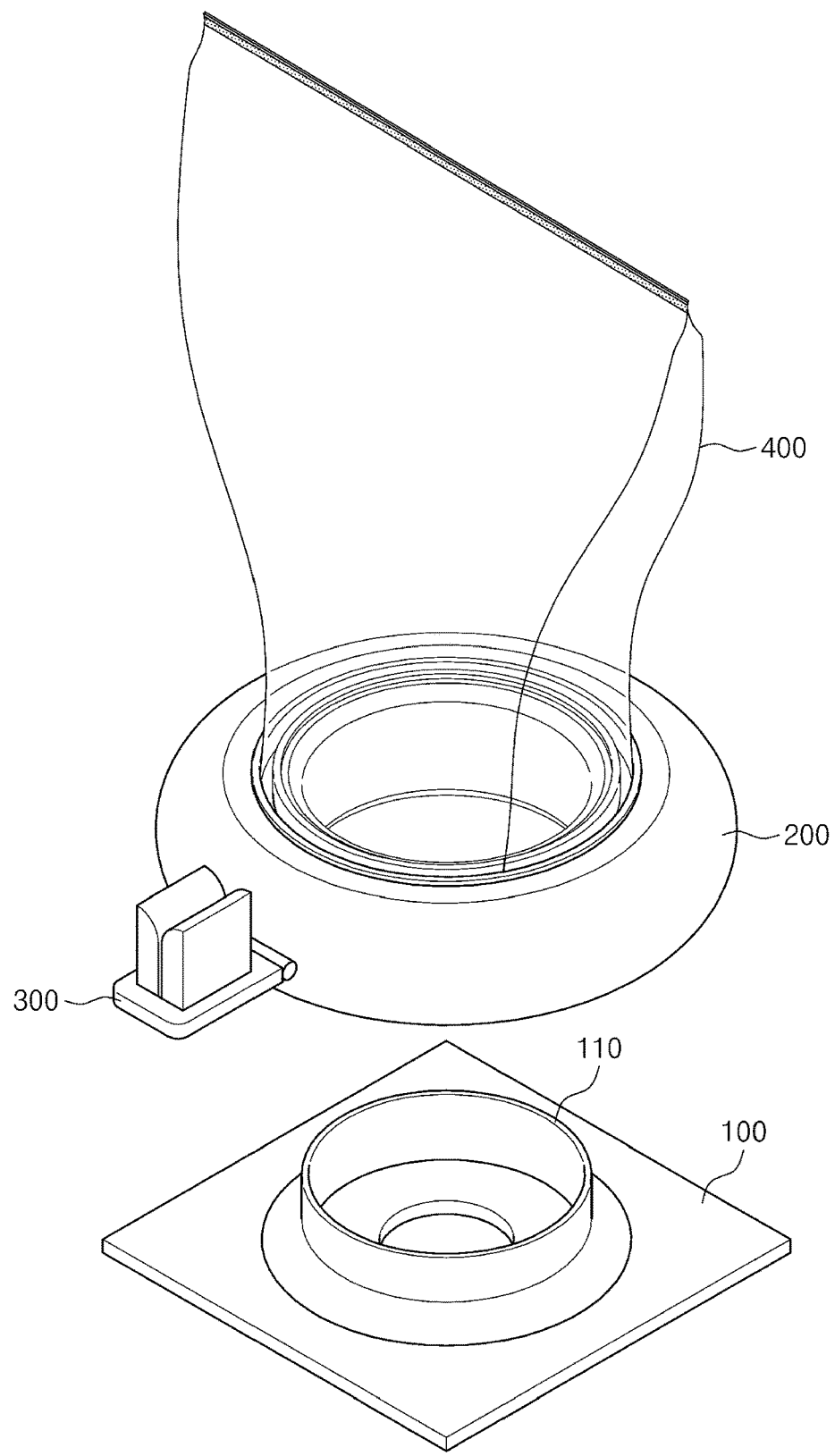
FIG. 1 is a schematic diagram for describing an ostomy appliance according to an embodiment of the present invention.

Hereinafter, detailed embodiments of the present invention will be described in detail with reference to the accompanying drawings.

In addition, in description of the present invention, when it is determined that the detailed description of widely known related configuration or function may make the subject matter of the present invention unclear, the detailed description will be omitted.

Embodiments of the present invention are provided to more completely describe the present invention to those skilled in the art, the following embodiments may be modified into various other forms, and the scope of the present invention is not limited to the following embodiments.

Rather, these embodiments are provided to make this disclosure be more thorough and complete and completely transfer the spirit of the present invention to those skilled in the art.

Further, in the following drawings, each component is exaggerated for convenience and clarity of description, and the same reference numerals refer to the same components on the drawings. In the present specification, a term "and/or" includes any one or all possible combinations of the listed items.

Terms used herein are used to describe specific embodiments, not to limit the present invention.

As used in the present specification, a singular form may include a plural form unless the context clearly indicates otherwise. Further, when used in the present specification, the terms "comprise" and/or "comprising" specify the presence of recited shapes, numbers, steps, actions, members, elements, and/or groups thereof, does not exclude the presence or addition of one or more other shapes, numbers, actions, members, and elements and/or groups.

Figure 2:
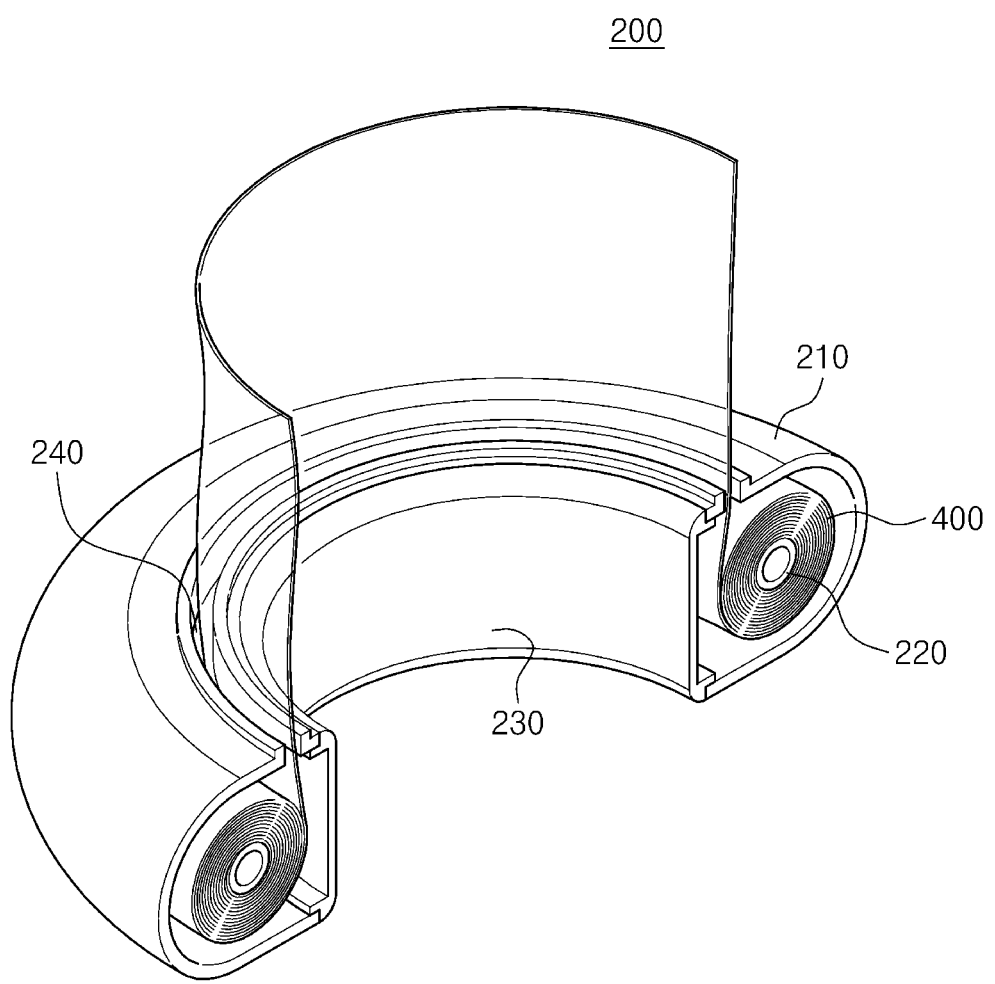
FIG. 2 is a cross-sectional view illustrating a cover assembly part of the ostomy appliance according to the embodiment of the present invention.
Figure 3:
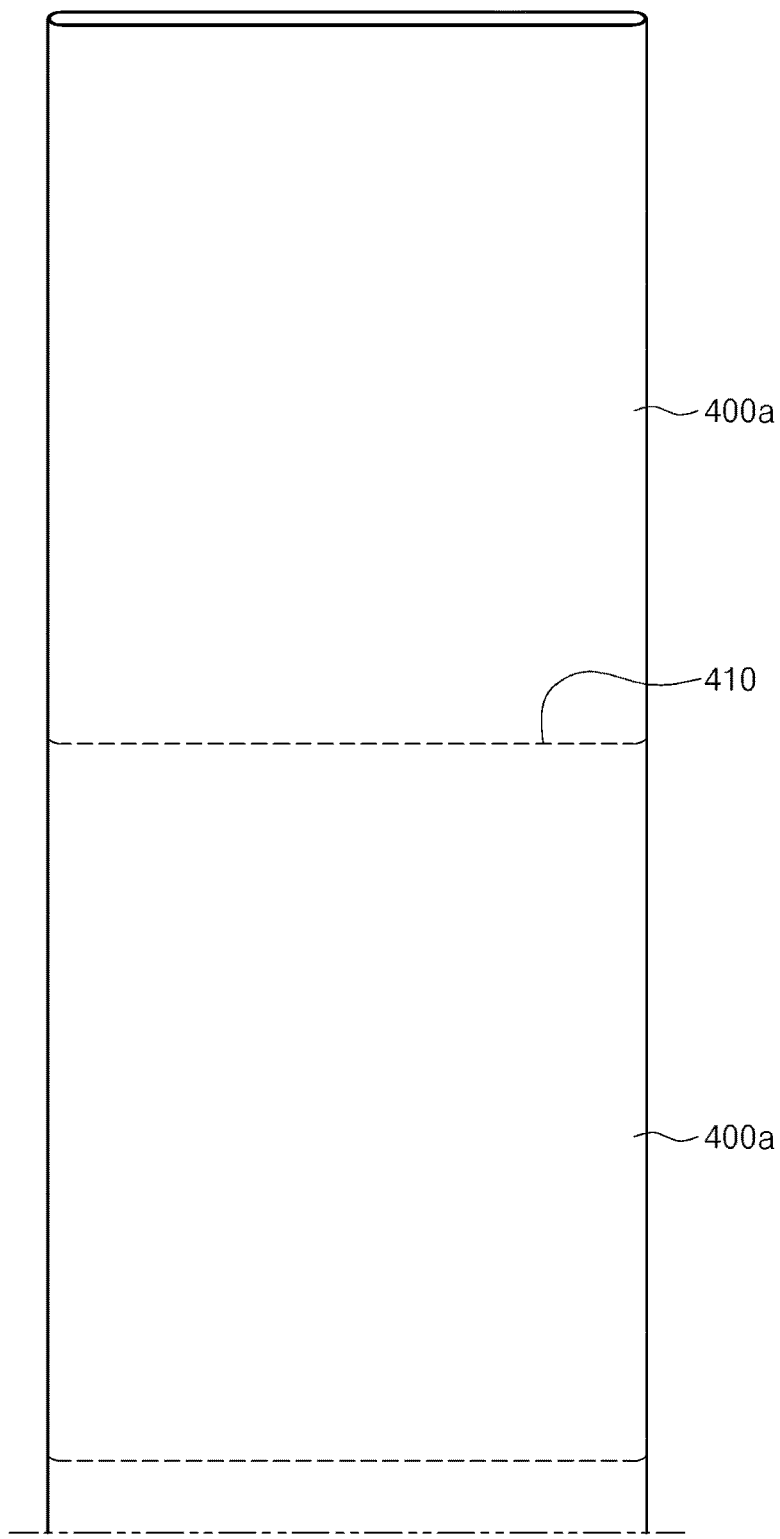
FIG. 3 is a view for describing a vinyl sheet discharged from the cover assembly part according to the embodiment of the present invention.
Figure 4:
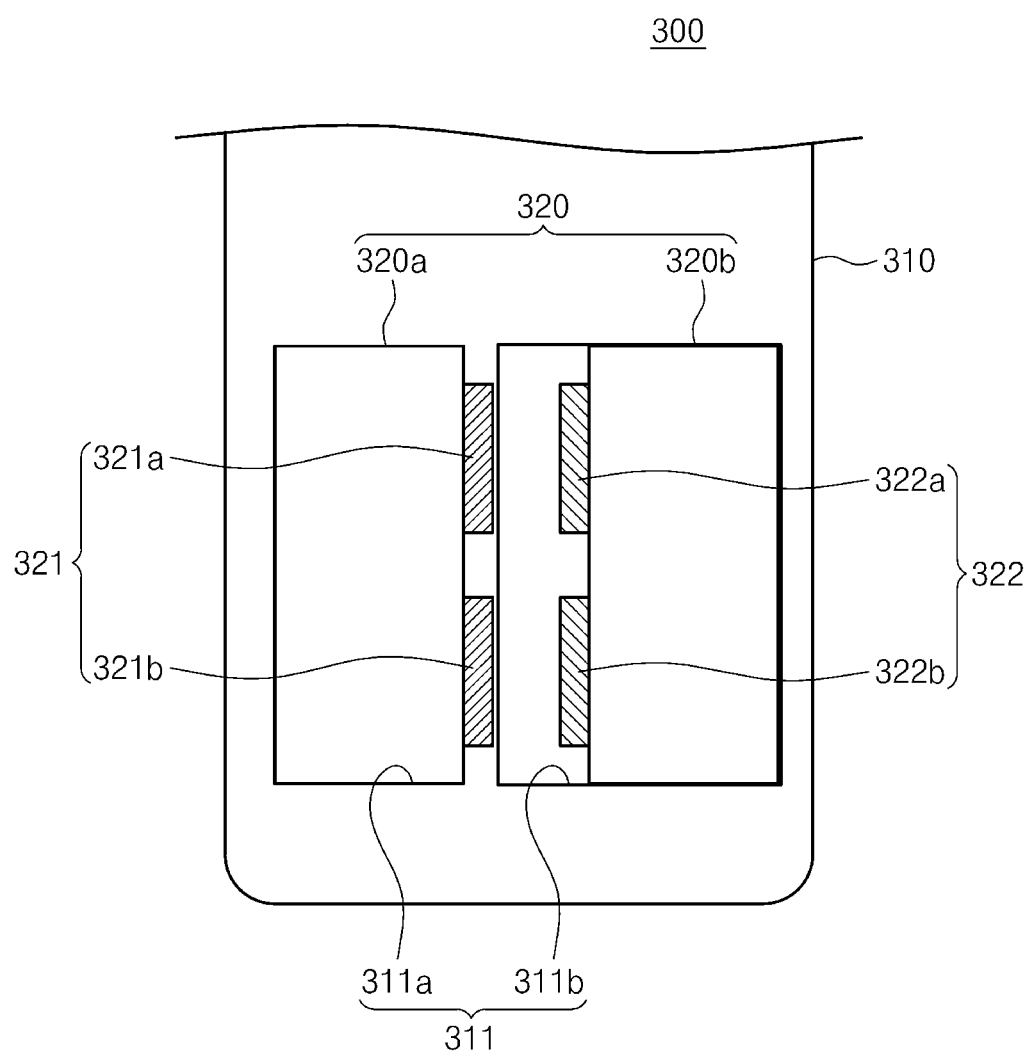
FIG. 4 is a plan view for describing a sealing part of the ostomy appliance according to the embodiment of the present invention.
Figure 5:
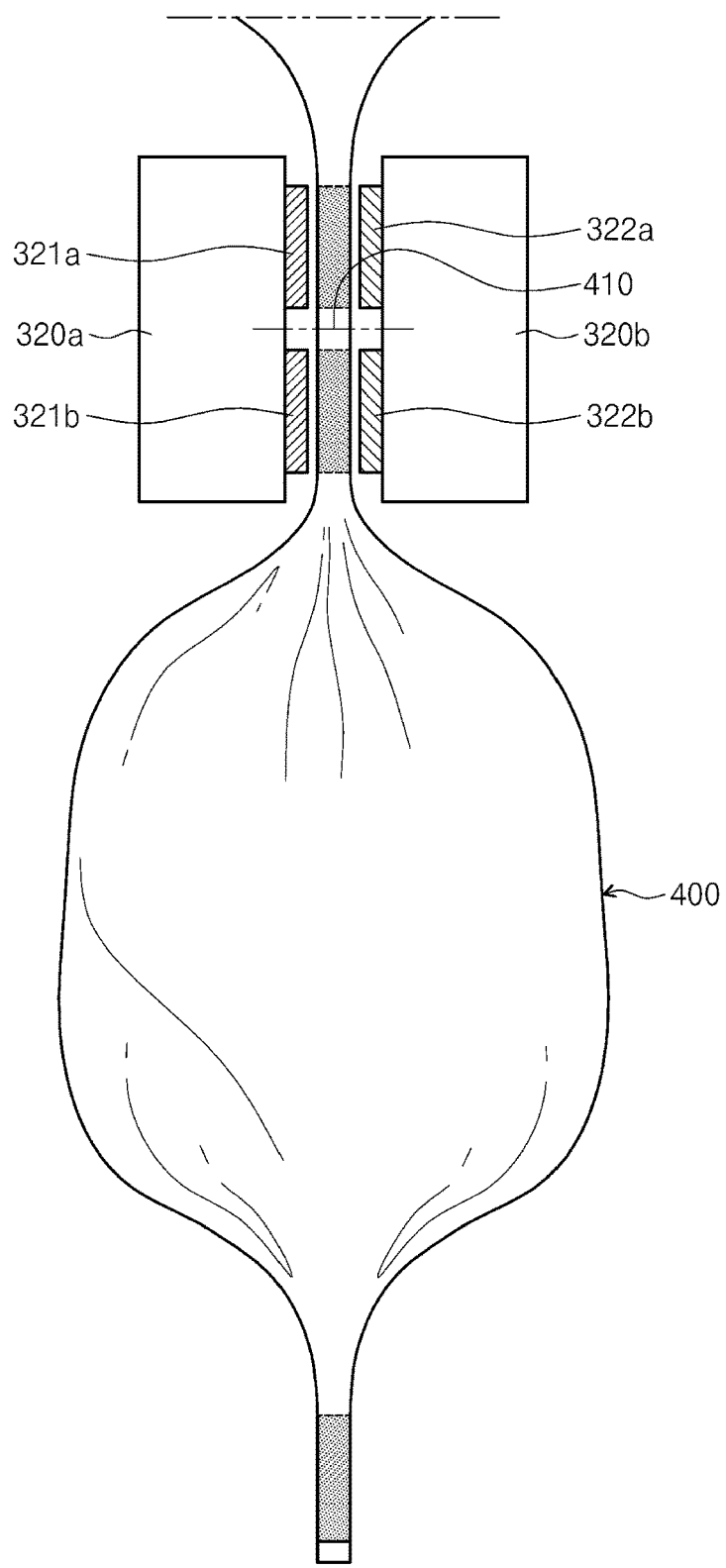
FIG. 5 is a view illustrating a process of heat-sealing the vinyl sheet discharged from the cover assembly part using the sealing part according to the embodiment of the present invention.

FIG. 1 is a schematic diagram for describing an ostomy appliance according to an embodiment of the present invention, FIG. 2 is a cross-sectional view illustrating a cover assembly part of the ostomy appliance according to the embodiment of the present invention, FIG. 3 is a view for describing a vinyl sheet discharged from the cover assembly part according to the embodiment of the present invention, FIG. 4 is a plan view for describing a sealing part of the ostomy appliance according to the embodiment of the present invention, and FIG. 5 is a view illustrating a process of heat-sealing the vinyl sheet discharged from the cover assembly part using the sealing part according to the embodiment of the present invention.

Referring to FIG. 1, the ostomy appliance according to an embodiment of the present invention includes an attachment part 100, a cover assembly part 200, and a sealing part 300.

The attachment part 100 may be attached to a skin of a user. In addition, the attachment part 100 is provided with an attachment unit such as an adhesive harmless to a human body and adheres to the skin. The attachment unit may be in the form of an attachment film that may be adapted to some extent even in bending of the skin or movement of the human body of the user.

Accordingly, the attachment part 100 may provide an adhesive force to prevent a vinyl sheet 400 into which excretion of the user is retracted due to the weight of the excretion from being separated from the user.

In detail, the attachment part 100 has a through-hole formed in the center thereof, is disposed to surround an ostomy of the user, and has a lower surface coated with an attachment film harmless to the human body. In addition, the attachment part 100 may use a harmless flexible material having a color similar to a skin color of the user to increase a sense of unity with the skin, thereby improving wearing comfort and activity.

Meanwhile, the attachment part 100 may further include a cylindrical cap portion 110 having a predetermined length.

It is preferable that the cap portion 110 be made of a material that guarantees waterproofness and s predetermined tensile strength, and the cap portion 110 is made of for example, a polymer material such as rubber.

Further, the cap portion 110 is detachably disposed around the through-hole formed in the attachment part 100. Likewise, a lower surface of the cap portion 100 may be coated with an attachment film and thus may be attached to an upper surface of the attachment part 100.

The cover assembly part 200 may be disposed on the upper surface of the attachment part 100, and the vinyl sheet 400 into which the excretion is retracted may be continuously discharged.

In addition, the cover assembly part 200 may be formed in a ring shape having a hollow in a center thereof and may be detachably disposed on the upper surface of the attachment part 100.

In detail, an inner edge portion of the cover assembly part 200 may be fitted in and detachably fixed to an outer circumferential surface of the cap portion 110.

Accordingly, the ostomy appliance according to the embodiment of the present invention may be a two-piece type ostomy appliance including the attachment part 100 serving as a skin barrier in a general ostomy appliance field and the cover assembly part 200 serving as a stoma bag containing defecation and urine, wherein the cover assembly part 200 is detachably attached to the attachment part 100.

Accordingly, in the ostomy appliance according to the embodiment of the present invention, when the cover assembly part 200 is no longer usable due to an end of the lifetime for any reason, the cover assembly part 200 is replaced newly, and thus the ostomy appliance may be used for a longer period of time than the one-piece type ostomy appliance.

Hereinafter, an ostomy appliance according to another embodiment of the present invention will be described with reference to FIG. 1. However, since another embodiment of the present invention is different from the embodiment of the present invention in that the cover assembly part 200 is integrally coupled to the attachment part 100, the difference is mainly described below, and corresponding parts refer to the description and reference numerals of the embodiment of the present invention.

The ostomy appliance according to another embodiment of the present invention may include the attachment part 100, the cover assembly part 200, and the sealing part 300, wherein the attachment part 100 further includes the cylindrical cap portion 110 having a predetermined length, and the cover assembly part 200 is integrally coupled to the attachment part 110.

In detail, in another embodiment of the present invention, the inner edge portion of the cover assembly part 200 and the outer circumferential surface of the cap portion 110 may be fixedly coupled using a well-known process such as welding or bonding so that the inner edge portion of the cover assembly part 200 and the outer circumferential surface of the cap portion 110 cannot be separated from each other.

Further, the attachment part 100 may be formed integrally with the cap portion 110 so that the cap portion 110 cannot be attached/detached, and accordingly, in the ostomy appliance according to another embodiment of the present invention, the attachment part 100, the cover assembly part 200, and the sealing part 300 may be integrated to form a single ostomy appliance.

Accordingly, the ostomy appliance according to another embodiment of the present invention may be a one-piece type ostomy appliance including the attachment part 100 serving as a skin barrier in a general ostomy appliance field and the cover assembly part 200 serving as a stoma bag containing defecation and urine, wherein the cover assembly part 200 is fixedly coupled to the attachment part 100.

Referring to FIG. 2, the cover assembly part 200 includes a body portion 210, a ring-shaped tube portion 220, and a cover portion 230.

The body portion 210 is a component constituting a body of the cover assembly part 200 and may have an inner space in a circumferential direction while being formed in a ring shape.

In addition, the body portion 210 may be formed in various shapes such as an elliptical shape and a polygonal shape according to the shape of the ostomy of the user and needs, and the shape thereof is not limited.

The ring-shaped tube portion 220 may be disposed in an inner space of the body portion 210 and the vinyl sheet 400 may be wound around the ring-shaped tube portion 220.

In addition, the ring-shaped tube portion 220 may be formed in a ring shape so that the vinyl sheet 400 may be discharged in a cylindrical shape and may be formed of a material such as silicone or rubber having flexibility.

The cover portion 230 may shield the inner edge portion of the body portion 210 and may guide the vinyl sheet 400 wound around the ring-shaped tube portion 220 such that the vinyl sheet 400 is discharged in an upward direction.

In detail, a discharge groove 240 may be formed between the body portion 210 and the cover portion 230 in a circumferential direction, and the wound vinyl sheet 400 is discharged to the discharge groove 240 through pulling of the user.

That is, the body portion 210 may accommodate the ring-shaped tube portion 220 and include an open region through which the vinyl sheet 400 wound around the ring-shaped tube portion 220 is discharged to the outside, and the cover portion 230 may block a portion of the open region except for a partial region of the open region to prevent water or foreign substances from being introduced into the open region.

Referring to FIG. 3, the vinyl sheet 400 wound around the ring-shaped tube portion 220 according to the present invention may have a plurality of unit vinyl sheets 400a having a substantially cylindrical structure when discharged from the cover assembly portion 200 and having both open ends in a longitudinal direction.

In detail, the vinyl sheet 400 is formed in a cylindrical shape in which an upper end and a lower end are open, may be folded flat and wound around the ring-shaped tube body 220, and is provided with perforated lines at preset intervals to be divided into the plurality of unit vinyl sheets 400a.

In addition, the unit vinyl sheets 400a may be continuously connected in the same standard so as to form the one vinyl sheet 400.

That is, when the excretion is retracted into one unit vinyl sheet 400a and the one unit vinyl sheet 400a is full of the excretion, the user may continuously use another unit vinyl sheet 400a using the perforated lines, and it is possible to solve a troublesome of washing the excretion or replacing the unit vinyl sheet 400a with a new ostomy bag like a general ostomy bag.

Further, the unit vinyl sheet 400a may be made of a polyethylene material that is deformed in shape by an operation of the user and maintains the shape thereof in the deformed state, but the present invention is not limited thereto, and the unit vinyl sheet 400a may be made of the same material as a general vinyl bag.

Further, an upper end of the unit vinyl sheet 400a may be joined by heat sealing in a circumferential direction. In detail, the upper end of the unit vinyl sheet 400a is joined, a lower end of the unit vinyl sheet 400a is opened so that an excretion storage space in which the excretion may be stored is formed, and when the excretion storage space is full, after the lower end of the unit vinyl sheet 400a is joined by heat sealing, the unit vinyl sheet 400a may be cut along the perforated line.

Referring to FIG. 4, the sealing part 300 may be coupled to one side of the cover assembly part 200 and may heat-seal a portion of the discharged vinyl sheet 400.

In detail, the sealing part 300 includes a sealing support portion 310 that is hinge-coupled to one side of an outer edge portion of the body portion 210 that is a component constituting the body of the cover assembly part 200 and rotates in a direction perpendicular to the body portion 210 and a sealing insulation portion 320 disposed at an upper end of the sealing support portion 310.

The sealing support portion 310 may be made of a plastic material that is light and has high strength and may be made of a metal material such as aluminum as needed.

Further, as illustrated in FIG. 1, the sealing support portion 310 may vertically rotate about the portion hinge-coupled to the cover assembly part 200 and freely move to a position adjacent the discharged vinyl sheet 400 according to an operation of the user.

The sealing insulation portion 320 is disposed at an upper end of the sealing support portion 310 and serves to transfer heat to the unit vinyl sheet 400a to heat-seal the unit vinyl sheet 400a.

In detail, the sealing insulation portion 320 may include a first sealing insulation portion 320a formed such that a heating portion 321 for heat-sealing a portion of the unit vinyl sheet 400a is mounted on one side surface thereof and a second sealing insulation portion 320b formed such that a pressing portion 322 positioned to be engaged with the heating portion 321 is mounted on a surface facing the one side surface of the first sealing insulation portion.

Further, the first sealing insulation portion 320a and the second sealing insulation portion 320b may be inserted into and disposed in a mounting groove 311 provided in the sealing support portion 310. In this case, the mounting groove 311 includes a first mounting groove 311a into which the first sealing insulation portion 320a is inserted and a second mounting groove 311b into which the second sealing insulation portion 320b is inserted.

In addition, the first mounting groove 311a is provided according to the standard of the first sealing insulation portion 320a so that the first sealing insulation portion 320a is fixedly fitted in the first mounting groove 311a.

In addition, the second mounting groove 311b is preferably provided larger than the size of the second sealing insulation portion 320b so that the second sealing insulation portion 320b may be fixedly fitted in the second mounting groove 311b and the second sealing insulation portion 320b may slide to move in a direction in which the second sealing insulation portion 320b approaches or moves away from the first sealing insulation portion 320a.

Further, arrangement grooves (not illustrated) into which the heating portion 321 and the pressing portion 322 are inserted and arranged are formed in the first sealing insulation portion 320a and the second sealing insulation portion 320b.

In this case, the heating portion 321 may be formed in a circular shape or rectangular shape and may be mounted in the arrangement groove to protrude more than one side surface of the first sealing insulation portion 320a.

In addition, the pressing portion 322 is formed to have the same shape as the heating portion 321 and is mounted on the arrangement groove to protrude more than one side surface of the second sealing insulation portion 320b.

As illustrated in FIG. 5, the heating portion 321 may be divided into a first heater 321a and a second heater 321b, which may be dividedly mounted in a central portion of the one side surface of the first sealing insulation portion 320a at a predetermined separation region.

In other words, the first heater 321a and the second heater 321b may be arranged adjacent to each other and arranged at preset separation distances, and accordingly, the vinyl sheet 400 may be joined while having a heat sealing area separated by a predetermined distance.

Likewise, the pressing portion 322 may be divided into a first pressing bar 322a and a second pressing bar 322b, which may be arranged apart from each other by the preset separation distance.

In more detail, the vinyl sheet is fitted in a gap between the first sealing insulation portion 320a and the second sealing insulation portion 320b, the perforated line of the inserted vinyl sheet 400 is positioned between the first heater 321a and the second heater 321b, and portions of the unit vinyl sheets 400a adjacent to each other with respect to the perforated line are simultaneously heat-sealed.

For example, the vinyl sheet 400 discharged from the cover assembly part 200 is used as an excretion storage space, and when the excretion storage space is full, the user pulls the vinyl sheet 400 by a sufficient length so that a next perforated line is visible, then presses a partial region of the adjacent unit vinyl sheets 400a with respect to the perforated line, and inserts the vinyl sheet into the gap between the first sealing insulation portion 320a and the second sealing insulation portion 320b.

Thereafter, the vinyl sheet 400 is rearranged so that the perforated line is located in a preset separation region of the first sealing insulation portion 320a, and the second sealing insulation portion 320b slides in a direction in which the second sealing insulation portion 320b approaches the first sealing insulation portion 320a.

In this case, the first pressing bar 322a and the second pressing bar 322b of the second sealing insulation portion 320b may press the first heater 321a and the second heater 321b of the first sealing insulation portion 320a in a state in which the vinyl sheet 400 is inserted therebetween.

Figure 6:
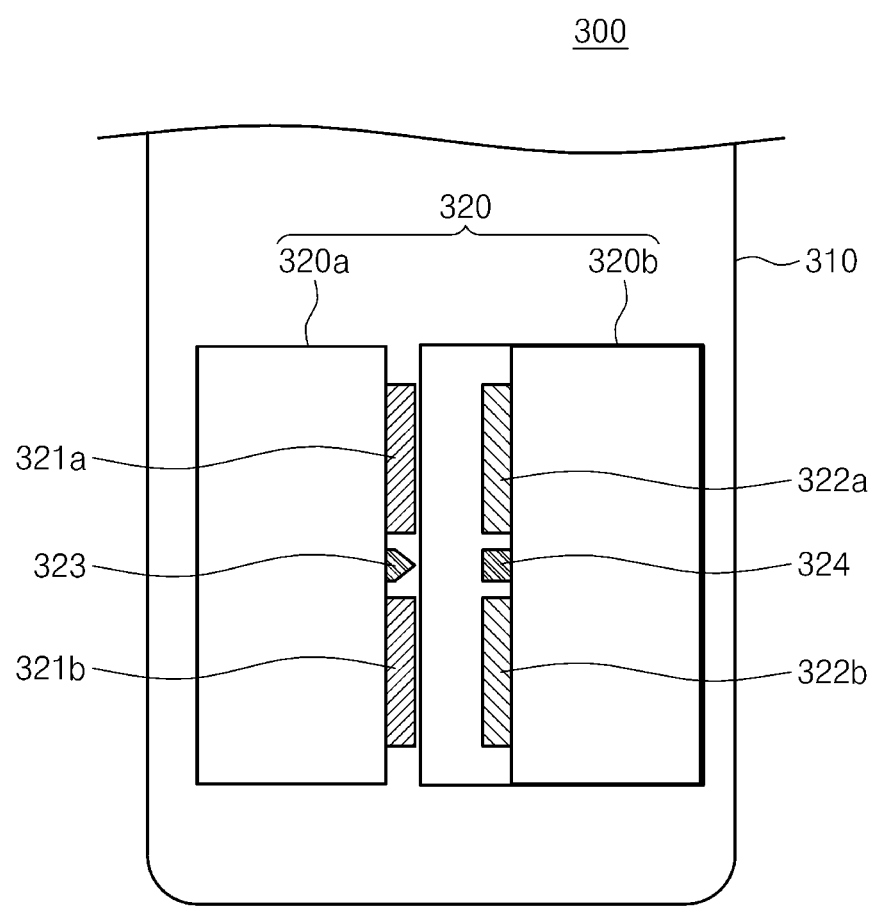
FIG. 6 is a plan view for describing a sealing part of an ostomy appliance according to another embodiment of the present invention.

FIG. 6 is a plan view for describing a sealing part of an ostomy appliance according to another embodiment of the present invention.

Referring to FIG. 6, the first sealing insulation portion 320a may further include a blade 323, and the second sealing insulation portion 320b may further include a stopper 324.

In detail, the second sealing insulation portion 320b slides in a direction of the first sealing insulation portion 320a, the blade 323 is engaged with the perforated line of the vinyl sheet 400, the vinyl sheet 400 is heat-sealed, at the same time, the vinyl sheet 400 is cut, and thus the unit vinyl sheet 400a may be made.

That is, as illustrated in FIG. 6, when the blade 323 is positioned in the first sealing insulation portion 320a, in a state in which the unit vinyl sheets 400a adjacent to each other with respect to the perforated line are heat-sealed, when the user wants to cut the vinyl sheet 400 along the perforated line of the vinyl sheet 400, burns caused by heat may be prevented.

The above detailed description exemplifies the present invention.

Furthermore, the above-mentioned contents describe the exemplary embodiment of the present invention, and the present invention may be used in various other combinations, changes, and environments. That is, the present invention may be modified and corrected without departing from the scope of the present invention that is disclosed in the specification, the equivalent scope to the written disclosures, and/or the technical or knowledge range of those skilled in the art. The written embodiment describes the best state for implementing the technical spirit of the present invention, and various changes required in the detailed application fields and purposes of the present invention may be made. Accordingly, the detailed description of the present invention is not intended to restrict the present invention in the disclosed embodiment state. Furthermore, it should be construed that the attached claims include other embodiments.

What is claimed is:

1. An ostomy appliance comprising:
   an attachment part attached to a skin of a user;
   a cover assembly part which is disposed on an upper surface of the attachment part and through which a vinyl sheet into which excretion is introduced is continuously discharged; and
   a sealing part coupled to one side of the cover assembly part and configured to heat-seal a portion of the discharged vinyl sheet.

2. The ostomy appliance of claim 1, wherein the cover assembly part is formed in a ring shape having a hollow in a center thereof and is disposed to be attached to or detached from the upper surface of the attachment part.

3. The ostomy appliance of claim 2, wherein the cover assembly part includes:
   a body portion having an inner space so that the vinyl sheet is accommodated;
   a ring-shaped tube portion which is disposed in the inner space of the body portion and around which the vinyl sheet is wound; and
   a cover portion configured to shield an inner edge portion of the body portion.

4. The ostomy appliance of claim 3, wherein a discharge groove is formed between the body portion and the cover portion in a circumferential direction, and the vinyl sheet is discharged through pulling of a user.

5. The ostomy appliance of claim 4, wherein the vinyl sheet is formed in a cylindrical shape in which an upper end and a lower end are open, is folded flat, and is wound around the ring-shaped tube portion, the vinyl sheet is provided with perforated lines at preset intervals and divided into a plurality of unit vinyl sheets, and the unit vinyl sheets are continuously connected in the same standard.

6. The ostomy appliance of claim 5, wherein the sealing part includes:

a sealing support portion hinge-coupled to one side of an outer edge portion of the body portion and rotated in a direction perpendicular to the body portion; and a sealing insulation portion disposed at an upper end of the sealing support portion.

7. The ostomy appliance of claim 6, wherein the sealing insulation portion includes:

a first sealing insulation portion formed such that a heating portion configured to heat-seal a portion of the unit vinyl sheet is mounted on one side surface thereof; and a second sealing insulation portion formed such that a pressing portion positioned to be engaged with the heating portion is mounted on a surface facing the one side surface of the first sealing insulation portion.

8. The ostomy appliance of claim 7, wherein the heating portion is mounted to protrude more than the one side surface of the first sealing insulation portion.

9. The ostomy appliance of claim 8, wherein the heating portion is divided into a first heater and a second heater which are dividedly mounted in a central portion of the one side surface of the first sealing insulation portion at a predetermined separation region.

10. The ostomy appliance of claim 9, wherein the vinyl sheet is fitted in a gap between the first sealing insulation portion and the second sealing insulation portion, and the perforated line of the fitted vinyl is positioned between the first heater and the second heater, and portions of the unit vinyl sheets adjacent to each other with respect to the perforated line are simultaneously heat-sealed.

11. The ostomy appliance of claim 10, wherein the cover assembly part is integrally coupled to the attachment part, and an inner edge portion of the cover assembly part and an outer circumferential surface of a cap portion included in the attachment part are fixedly coupled using welding or bonding so that the inner edge portion of the cover assembly part and the outer circumferential surface of the cap portion are not separated from each other.

* * * * *